United States Patent
Liu et al.

(10) Patent No.: US 9,327,271 B2
(45) Date of Patent: May 3, 2016

(54) CATALYTIC CONVERSION OF CARBOHYDRATES INTO 5-HYDROXYMETHYLFURFURAL

(71) Applicant: DALIAN INSTITUTE OF CHEMICAL PHYSICS, CHINESE ACADEMY OF SCIENCES, Dalian, Liaoning Province (CN)

(72) Inventors: Qishun Liu, Dalian (CN); Heng Yin, Dalian (CN); Yuguang Du, Dalian (CN); Fengli Yang, Dalian (CN); Wenxia Wang, Dalian (CN)

(73) Assignee: DALIAN INSTITUTE OF CHEMICAL PHYSICS, CHINESE ACADEMY OF SCIENCES, Dalian, Liaoning (CN)

( * ) Notice: Subject to any disclaimer, the term of this patent is extended or adjusted under 35 U.S.C. 154(b) by 43 days.

(21) Appl. No.: 14/308,391

(22) Filed: Jun. 18, 2014

(65) Prior Publication Data

US 2014/0302982 A1    Oct. 9, 2014

Related U.S. Application Data

(62) Division of application No. 13/863,925, filed as application No. PCT/CN2010/079290 on Nov. 30, 2010, now Pat. No. 8,785,668.

(30) Foreign Application Priority Data

Nov. 29, 2010    (CN) .......................... 2010 1 0563786

(51) Int. Cl.
| | | |
|---|---|---|
| B01J 29/00 | (2006.01) | |
| B01J 29/04 | (2006.01) | |
| B01J 29/06 | (2006.01) | |
| B01J 21/00 | (2006.01) | |
| B01J 21/04 | (2006.01) | |
| B01J 23/00 | (2006.01) | |
| B01J 23/02 | (2006.01) | |
| B01J 23/08 | (2006.01) | |
| B01J 23/20 | (2006.01) | |
| C07D 307/48 | (2006.01) | |
| C07D 307/50 | (2006.01) | |
| C07D 307/44 | (2006.01) | |
| B01J 37/03 | (2006.01) | |
| B01J 37/06 | (2006.01) | |
| B01J 21/06 | (2006.01) | |
| B01J 23/26 | (2006.01) | |
| B01J 37/00 | (2006.01) | |

(52) U.S. Cl.
CPC ............... B01J 23/20 (2013.01); B01J 21/066 (2013.01); B01J 23/26 (2013.01); B01J 37/0018 (2013.01); B01J 37/0036 (2013.01); B01J 37/031 (2013.01); B01J 37/06 (2013.01); C07D 307/44 (2013.01); C07D 307/48 (2013.01); C07D 307/50 (2013.01)

(58) Field of Classification Search
CPC ...... B01J 29/064; B01J 29/068; B01J 29/072; B01J 29/076; B01J 23/20; B01J 23/64; B01J 23/84; B01J 23/898; B01J 21/04; B01J 21/06; B01J 21/08; B01J 21/12
USPC ............... 502/66, 74, 87, 246, 311, 313–315, 502/349, 353, 354, 355, 415, 439
See application file for complete search history.

(56) References Cited

U.S. PATENT DOCUMENTS

| | | | | |
|---|---|---|---|---|
| 3,865,873 | A | * | 2/1975 | Oda .......................... B01J 23/28 502/211 |
| 4,171,320 | A | * | 10/1979 | Vannice .................. B01J 23/462 502/325 |
| 4,184,981 | A | * | 1/1980 | Vanderspurt ............. B01J 23/28 502/209 |
| 4,195,187 | A | * | 3/1980 | Vanderspurt ............. B01J 23/28 502/209 |
| 4,206,135 | A | * | 6/1980 | Kugler ................... B01J 23/755 502/185 |
| 4,221,768 | A | * | 9/1980 | Inoue .................... B01D 53/945 423/213.2 |
| 4,233,139 | A | * | 11/1980 | Murrell .................... B01J 23/20 208/112 |
| 4,244,811 | A | * | 1/1981 | Grenoble ................ C01B 3/363 208/118 |
| 4,269,737 | A | * | 5/1981 | Grenoble ................. B01J 21/06 502/202 |
| 4,415,480 | A | * | 11/1983 | Murrell .................... B01J 23/20 502/242 |

(Continued)

FOREIGN PATENT DOCUMENTS

WO    2010/101024 A1    9/2010

OTHER PUBLICATIONS

Garbine Guiu, et al. "Acidic and Catalytic Properties of SiO2—Ta2O5 Mixed Oxides Prepared by the Sol-Gel Method." Journal of Catalysis 156, pp. 132-138 (1995).

(Continued)

Primary Examiner — Cam N. Nguyen
(74) Attorney, Agent, or Firm — Novick, Kim & Lee, PLLC; Allen Xue

(57) ABSTRACT

The present invention relates to catalysts and methods for efficient conversion of carbohydrates into 5-hydroxymethylfurfural (HMF), which shows good activity and high selectivity for HMF preparation from saccharides. The catalyst is stable in aqueous system which makes it as an ideal catalyst for HMF production. High HMF yield was obtained even in mild condition. The catalysts of the invention are advantageous in that they are environment-friendly, easy separation and recovery, can be re-used in subsequent reactions, do not corrode reaction reactors. These features make the catalyst as a suitable catalyst for HMF preparation and have strong industrial application significance.

13 Claims, No Drawings

(56) References Cited

U.S. PATENT DOCUMENTS

| | | | | |
|---|---|---|---|---|
| 4,424,163 A * | 1/1984 | Rosen | | C11C 3/123 502/337 |
| 4,469,804 A * | 9/1984 | Johnson | | B01J 27/32 502/224 |
| 4,544,649 A * | 10/1985 | Wachs | | B01J 23/20 502/350 |
| 4,582,911 A * | 4/1986 | Wachs | | B01J 23/20 502/350 |
| 4,711,871 A * | 12/1987 | Wachs | | B01J 23/648 502/325 |
| 4,748,145 A * | 5/1988 | Wood | | B01J 23/40 502/242 |
| 4,791,092 A * | 12/1988 | Wachs | | B01J 23/20 502/350 |
| 4,861,747 A * | 8/1989 | Wachs | | B01J 23/648 502/325 |
| 4,973,569 A * | 11/1990 | Bowman | | C07D 295/023 502/209 |
| 5,169,821 A * | 12/1992 | Soled | | B01J 21/063 502/242 |
| 5,182,249 A * | 1/1993 | Wang | | B01D 53/945 423/213.2 |
| 5,225,600 A * | 7/1993 | King | | C07C 209/16 502/308 |
| 5,496,532 A * | 3/1996 | Monzen | | C01B 15/029 423/584 |
| 6,171,571 B1 * | 1/2001 | Bedard | | B01J 23/002 423/508 |
| 6,428,765 B1 * | 8/2002 | Bedard | | B01J 23/002 208/134 |
| 6,521,566 B1 * | 2/2003 | Magno | | B01J 21/06 502/325 |
| 6,686,310 B1 * | 2/2004 | Kourtakis | | B01J 23/44 502/234 |
| 7,005,403 B2 * | 2/2006 | Borgmeier et al. | | 502/312 |
| 7,038,082 B2 * | 5/2006 | Borgmeier et al. | | 562/598 |
| 7,214,822 B2 * | 5/2007 | Borgmeier et al. | | 562/549 |
| 7,304,180 B2 * | 12/2007 | Tu et al. | | 562/547 |
| 7,491,676 B2 * | 2/2009 | Augustine et al. | | 502/353 |
| 7,524,792 B2 * | 4/2009 | Dieterle et al. | | 502/311 |
| 7,572,751 B2 * | 8/2009 | Isogai | | B01D 53/945 502/302 |
| 7,608,558 B2 * | 10/2009 | Eijsbouts et al. | | 502/222 |
| 7,691,777 B2 * | 4/2010 | Isogai | | B01D 53/945 423/263 |
| 7,776,782 B2 * | 8/2010 | Werpy | | B01J 21/18 502/182 |
| 7,989,386 B2 * | 8/2011 | Schmidt | | 502/223 |
| 8,034,742 B2 * | 10/2011 | Isogai | | B01D 53/944 502/302 |
| 8,075,859 B2 * | 12/2011 | Fu | | B82Y 30/00 423/239.1 |
| 8,173,306 B2 * | 5/2012 | Mizutani et al. | | 429/400 |
| 8,211,825 B2 * | 7/2012 | Mei et al. | | 502/339 |
| 8,633,131 B2 * | 1/2014 | Lee | | B01J 21/04 429/400 |
| 2005/0131255 A1 * | 6/2005 | Benderly et al. | | 562/546 |
| 2009/0281338 A1 | 11/2009 | Sanborn | | |
| 2010/0094070 A1 * | 4/2010 | Qiu et al. | | 585/513 |

OTHER PUBLICATIONS

Takashi Ushikubo, et al. "Catalytic properties of hydrated tantalum oxide." Applied Catalysis 67, pp. 25-38 (1990).

Yongsheng Chen, et al. "Supported Tantalum Oxide Catalysts: Synthesis, Physical Characterization, and Methanol Oxidation Chemical Probe Reaction." J. Phys. Chem. B. 107, pp. 5243-5250 (2003).

Takashi Ushikubo, et al. "Hydrated Tantalum Oxide as a Solid Acid Catalyst." Chemistry Letters, pp. 1573-1574 (1988), The Chemical Society of Japan.

Takashi Ushikubo. "Recent topics of research and development of catalysis by niobium and tantalum oxides." Catalysis Today 57, pp. 331-338 (2000).

Li-Zhi Tao, et al. "Sustainable production of acrolein: catalytic performance of hydrated tantalum oxides for gas-phase dehydration of glycerol." Green Chemistry. Published online Jan. 14, 2013, on http://pubs.rsc.org by Royal Society of Chemistry.

* cited by examiner

CATALYTIC CONVERSION OF CARBOHYDRATES INTO 5-HYDROXYMETHYLFURFURAL

CROSS-REFERENCE TO RELATED APPLICATIONS

This application is a divisional application to U.S. patent application Ser. No. 13/863,925, filed Apr. 16, 2013, now U.S. Pat. No. 8,785,668, issued Jul. 22, 2014.

FIELD OF THE INVENTION

This invention relates to producing HMF efficiently in the presence of a heterogeneous acid catalyst, i.e. the saccharides from biomass (such as hexose or hexose-rich biomass) are converted efficiently by solid acid catalyst, and the catalyst is recyclable, non-corrosive to equipment, environment-friendly, which make the process have a strong industrial significance.

BACKGROUND OF THE INVENTION

HMF is an important furan compound. A large amount of materials and chemical intermediates can be made from HMF, which is reactive due to the reactive aldehyde group and hydroxymethyl group in molecule of HMF. And it is expected that HMF will become a new platform chemical. Moreover, HMF is an important intermediate between biomass-derived chemicals and petroleum-derived chemicals, since it can be produced from biomass and then converted to 2,5-dimethylfuran or hydrocarbon. So it will relieve the growing tension of the oil resources to a certain degree. It is reported that 2,5-dimethylfuran has a great potential to replace fossil fuels because it has many excellent properties as biofuel, such as high energy density and boiling point than that of bio-ethanol (Kunkes E L, Simonetti D A, Dumesic J A, et al. Catalytic Conversion of Biomass to Monofunctional Hydrocarbons and Targeted Liquid-Fuel Classes[J]. Science 2008 322:417-421). In addition, 2,5-diformyfuran and 2,5-furandicarboxylic acid can also be obtained from HMF by oxidation. Wherein 2,5-diformyfuran can be used as starting material for synthesis of pharmaceuticals, polymer precursor and others chemicals, and 2,5-furandicarboxylic acid has a large potential as a replacement for terephthalic acid, which is obtained from fossil resources and widely used as a component in various polyesters, such as polyethylene terephthalate (PET) and polybutyleneterephthalate (PBT) (Pentz K W. *Br. Pat.* 2131014, 1984; Werpy T, Petersen G. *Top Value Added Chemicals From Biomass,* 2004). Additionally, HMF can be used as a pharmaceutical intermediate and flavor additive in cosmetic industry.

As a chemical platform, HMF has important applications in many industries, and more attention has been paid to it. Generally, HMF can be obtained by hexose dehydration under acidic catalyst. The reactant can be hexose, or oligosaccharides and glycans, even the biomass. The study of hexose dehydration into HMF is quite mature. According to the catalyst and reaction system, the reaction system can be divided into homogeneous catalysis system, ionic liquid system and heterogeneous catalysis system. In the homogeneous catalysis, some protonic acid such as HCl, $H_3PO_4$, $H_2SO4$ and some organic acids such as formic acid, levulinic acid are usually used as catalysts. However, the process associated with the problem of high corrosion, difficulty of separation and recovery, use of large amount of catalyst and so on. Thus more attention has been paid to ionic liquids system, and good HMF yields can be obtained in this reaction system. However, the high prices of ionic liquids and its unknown toxicity have limited the industrial application. The heterogeneous catalysis is one important part of catalytic disciplines for the easy separation and recovery of catalyst and environmental friendly. Now the problem about heterogeneous catalysis is that some solid acid such as zeolites is unstable in aqueous, i.e., the structure is easy to collapse, resulting in the decrease of catalytic activity. While the catalyst used in the present invention is stable in aqueous system, and its acidic strength will be enhanced. As natural green solvent, water is a good reaction medium for its low price which is desirable solvent for most of industrial production.

SUMMARY OF THE INVENTION

The present invention is to provide a simple method of manufacturing HMF from hexose or sugar-based carbohydrates. The process of the present invention provides an environment-friendly method for producing HMF with high rates of conversion and high selectivity using solid acid. The solid acid catalyst of the invention are advantageous in that they are easily separated from the reaction products, can be re-used in subsequent reactions, do not corrode reaction vessels or reactors and have a reduced environmental impact.

In order to achieve the above objects, the technical solutions adopted in the present invention are as follows:

This invention relates to a process of high efficient catalytic conversion of monosaccharides or polysaccharides into HMF catalyzed in the presence of a solid acid catalyst. The catalyst is tantalum-containing compound, which catalyze the monosaccharide and polysaccharide or biomass giving HMF yield of 40%-100% under 60° C.-300° C.

The catalyst used is tantalum hydroxide or tantalum salts and so on. Hydrated tantalum oxide or tantalum hydroxide is treated by inorganic acids, wherein inorganic acids include: sulfuric acid, phosphoric acid, nitric acid, etc.; the concentration of inorganic acid is from 0.1 to 10 mol/L. The treatment time is from 1 hour to 1 week.

Tantalum-containing compounds are the composite oxide or salts consisting of tantalum and other metal which have a specific structure. "Other metals" refer to nickel, tungsten, titanium, zirconium, chromium, aluminum, cobalt, platinum, palladium, ruthenium, molybdenum, vanadium, tin, etc. Typically, the amount of the metals used is from about 0.1% to about 50% of the tantalum compound. The tantalum compound may also be supported on a catalyst support, said catalyst support being selected from the various types of zeolite, silica, alumina, titania, zirconia, etc. And the mass ratio of tantalum compound to support is approximately from 0.001 to 1. The catalyst of the invention is calcinated at temperature from 100° C. to 1000° C. for activation (preferred 5 minutes or more).

"Reactant" is fructose, glucose, galactose, mannose, sucrose, starch, inulin, corn juice, cellulose and juice of Jerusalem artichoke tubers.

The reaction systems used are aqueous system, biphasic system consisting of water and organic solvents or miscible system, anhydrous systems. "Organic solvents" are insoluble in water but can be dissolved HMF, which are methyl isobutyl ketone, n-butanol, 2-butanol, tetrahydrofuran, ethyl acetate, dichloromethane, chloroform, acetone, and combinations thereof at any proportion. The volume ratio of water to organic solvent is from 1:20 to 20:1.

The reaction can be processed in anhydrous system, and the solvents are dimethyl sulfoxide, dimethyl formamide, dimethylacetamide, pyrrolidone, and combinations thereof in any proportion.

The process of the invention is performed at temperature from 60° C. to 300° C., and the reaction time from 10 min to 300 min.

The concentration of reactants is from 0.5% to 70%, and the amount of catalyst used is from 1:1 to 1:10000 by weight of the reactants.

The process of the present invention is carried out in high-pressure reactor. And the mixture of solvents with reactants and catalyst are put in the reactor which is preheated for 30 min, and then the reactor was stirred at a constant speed in order to promote the HMF formation. Herein, the solvents comprise of water and/or organic solvents such as butanol, 2-butanol, methyl isobutyl ketone or the mixture of them, and the reactants refer to hexose or hexose-based biomass.

The reaction temperature of the process is from 60° C. to 300° C., and the reaction time is from 10 min to 300 min, the stirring speed from 300 rpm to 1000 rpm. The hexose used in the process of the invention is fructose, glucose, mannose or galactose; the hexose-base biomass refers to biomass containing fructose, glucose, mannose, galactose, or inulin, corn syrup, starch, cellulose, Jerusalem artichoke powder. Fructose, inulin and Jerusalem artichoke juice are preferred.

The present invention has the following advantages:
1. Compared with the traditional process for producing HMF using soluble mineral acid as catalyst, the process in the present invention provides a novel, environmentally friendly method for producing HMF with high efficiency, high selectivity using solid acid. The solid acid catalysts of the invention are advantageous in that it is easily separated from the reaction products, can be re-used in subsequent reactions, do not corrode reactors. The catalyst in the invention is easily prepared and low-cost.
2. The reaction mediums used in the present invention are natural water or mixture-containing water. High selectivity of HMF has been obtained, and the process is environmental-friendly, moderate, simple and low-cost.
3. The dehydration of saccharides into HMF is occurred in the aqueous phase, and the formed HMF is extracted timely to organic phase by stirring. During this process, it will not only promote the dehydration of sugar into HMF in aqueous phase, but also avoid the side reaction of rehydration to occur and reduce the side products such as humins formation, which prevent the catalyst from deactivation. And the conversion rate of the reactant and HMF yield will be improved.
4. Biomass can be directly used as feedstock to produce bio-energy and bio-chemicals in the present invention, which make the process green and high yield. This process technology is similar with the existing petrochemical process, which make it have great industrial prospects and strategic significance.

In summary, the reaction procedure of the present invention has high HMF selectivity and environment-friendly using solid acid as catalyst. The reaction condition is moderate and the process simple. The reuse of the catalyst reduces the cost, which provides a new way for preparing HMF from biomass in large scale. And the catalyst is beneficial to prepare the substitute of petroleum-based chemicals and alternative fuels using biomass as feedstock, which has a strong practical significance to the society.

EXAMPLES

Examples 1

A flask was charged with 1.5 g of tantalum hydroxide and 20 ml 1 M $H_3PO_4$, and the mixture was stirred for 52 h at room temperature, then aged for 12 h. The white precipitate was gained by centrifugation, which was washed by water until the pH of the solution became neutral. Then the precipitate was ground and dried under 60° C. for 12 h and 110° C. for 2 h in a vacuum oven. Finally, the precipitate was slowly heated to 300° C. for 3 h in a muffle furnace. And the catalyst labeled as TA-p was obtained.

A 100 ml high-pressure reactor was charged with 0.01 g of TA-p catalyst, 1.2 g of glucose, 20 ml of water and 30 ml methyl isobutyl ketone. And the reactor was sealed and heated to 160° C. for 30 min. The reactor was then cooled, and the catalyst was separated by filtration. The solution was analyzed by high performance liquid chromatography (HPLC). The HMF yield was 78%.

Examples 2

A flask was charged with 1 g of tantalum pentachloride and 10 ml of mathanol. 0.2 g of zirconium oxychloride was added to the mixture after the tantalum pentachloride dissolved. Then ammonia was dropped under stirring until the pH became neutral. The mixture was stirred for 4 h and aged for 12 h, then washed by water until no $Cl^-$ detection. The obtained precipitate was dried at 60° C. for 2 h then 500° C. for 3 h. The catalyst was labeled as 20% $ZrO/Ta_2O_5$, and then characterized by XPS.

A 100 ml high-pressure reactor was charged with 0.1 g of $ZrO/Ta_2O_5$, 2 g of fructose, 20 ml of water and 30 ml of 2-butanol. And the reactor was sealed and heated to 160° C. for 60 min. The reactor was then cooled, and the catalyst was separated by filtration. The solution was analyzed by HPLC. The HMF yield was 89%.

Examples 3

A flask was charged with 0.2 g of tantalum pentachloride and 20 ml of ethanol. 2 g of silica was added to the mixture after the tantalum pentachloride dissolved. The mixture was stirred for 3 h and aged for 5 h. The precipitate was gained by centrifugation which was washed by water until no $Cl^-$ detection. Finally, the precipitate was dried under 450° C. The 10% $Ta_2O_5/SiO_2$ as catalyst was obtained.

A 100 ml high-pressure reactor was charged with 0.1 g of $Ta_2O_5/SiO_2$, 1.4 g of fructose, 10 ml of water and 40 ml of methyl isobutyl ketone. And the reactor was sealed and reacted at 160° C. for 45 min. The reactor was then cooled, and the catalyst was separated by filtration. The solution was analyzed by HPLC. The HMF yield was 82%.

Examples 4

A 100 ml high-pressure reactor was charged with 0.1 g of TA-p, 2 g of inulin and 50 ml of dimethylsulfoxide. And the reactor was sealed and reacted at 160° C. for 150 min under stirring. The reactor was then cooled, and the catalyst was separated by filtration. The solution was analyzed by HPLC. The HMF yield was 85%.

Examples 5

A 100 ml high-pressure reactor was charged with 0.1 g of TA-p, 10 ml of corn juice (total sugar concentration of 50%), 10 ml of water and 30 ml of 2-butanol. And the reactor was sealed and reacted at 180° C. for 150 min under stirring at 800 rpm. The reactor was then cooled, and the catalyst was separated by filtration. The solution was analyzed by HPLC. The HMF yield was 55%.

Examples 6

A 100 ml high-pressure reactor was charged with 0.1 g of tantalum hydroxide, 10 ml of Jerusalem artichoke juice (12 wt %), 10 ml of water and 30 ml of 2-butanol. And the reactor was preheated for 30 min., then sealed and reacted at 160° C. for 90 min under stirring at 800 rpm. The reactor was then cooled, and the catalyst was separated by filtration. The solution was analyzed by HPLC. The HMF yield was 71%.

Examples 7

A flask was charged with 3 g of tantalum pentachloride and dropped with aqueous ammonia to precipitate, and then the pH was adjusted to neutral. After that the mixture was stirring for 5 h and aged for overnight. The obtained precipitate was washed with water until no chlorine ions were detected. Finally, the precipitate was calcined at 350° C., and the desired tantalum hydroxide was obtained.

A 100 ml high-pressure reactor was charged with 0.1 g of the prepared tantalum hydroxide, 1.2 g of fructose, 20 ml of water and 30 ml of 2-butanol, and the mixture was reacted at 160° C. for 40 min under stirring at 800 rpm. The solution was analyzed by HPLC. The HMF yield was 91%.

Examples 8

A vessel was charged with 0.2 g of tantalate chromium potassium, 2.0 g of fructose and 30 ml of pyrrolidone. The mixture was reacted at 80° C. for 2 h, and then the solution was analyzed by HPLC. The HMF yield was 70%.

Examples 9

A 100 ml high-pressure reactor was charged with 0.1 g of the tantalum hydroxide treated with 1 M $H_3PO_4$ and calcined at 600° C., 3 g of starch, 20 ml of water and 30 ml of methyl isobutyl ketone. And the mixture was reacted at 180° C. for 1.5 h. The solution was analyzed by HPLC. The HMF yield was 42%.

Examples 10

A 100 ml high-pressure reactor was charged with 0.1 g of the tantalum hydroxide treated with 1 M $HNO_3$ and calcined at 450° C., 3 g of inulin, 20 ml of water and 30 ml of 2-butanol. And the mixture was reacted at 150° C. for 2 h and the solution was analyzed by HPLC. The HMF yield was 54%.

Examples 11

A 100 ml high-pressure reactor was charged with 0.05 g of the tantalum hydroxide treated with 1 M $H_3PO_4$ and calcined at 300° C., 3 g of Jerusalem artichoke tuber and 30 ml of N,N-dimethylacetamide. The mixture was reacted at 100° C. for 2 h under stirring. The solution was analyzed by HPLC. The HMF yield was 65% (based on the total saccharides of the Jerusalem artichoke powder).

In the above experiments, the catalyst can be reused for three times and its activity did not decline.

As can be seen from the above embodiments, the present invention provides a method of producing HMF efficiently from hexose or hexose-based biomass, and the process is carried out in a biphasic system of water and organic solvents in the presence of solid acid of tantalum compound. High yield of HMF can be obtained under mild condition. Compared with other solid acid and liquid acid catalysis technology, there are many advantages in the present invention: high reactant conversion rate, high HMF selectivity, low cost of catalyst, easy to separate and re-use, no corrosion to reactor. The solid present in this invention is an ideal solid acid for preparing HMF since the low-cost catalyst shows good catalytic performance under mild condition.

What is claimed is:

1. A tantalum-containing catalyst, comprising:
    a tantalum-containing compound chosen from tantalates, tantalum oxides, or mixtures thereof; and one or more metal oxides, wherein the metal in the metal oxides is selected from the group consisting of nickel, tungsten, titanium, zirconium, aluminum, cobalt, platinum, palladium, ruthenium, molybdenum, vanadium, tin, and niobium,
    wherein the tantalates and the tantalum oxides are produced by a method comprising reacting hydrated tantalum oxide or tantalum hydroxide with an inorganic acid to obtain a precipitate; and calcining the precipitate,
    wherein the inorganic acid is hydrochloric acid, sulfuric acid, phosphoric acid, or nitric acid,
    wherein the molar ratio of the one or more metals to tantalum is from 1:2.5 to 1:100.

2. The tantalum-containing catalyst of claim 1, wherein the tantalum-containing catalyst is not supported on a catalyst carrier.

3. The tantalum-containing catalyst of claim 1, wherein a concentration of the inorganic acid ranges from 0.1 mol/L to 10 mol/L.

4. The tantalum-containing catalyst of claim 1, wherein said tantalum-containing catalyst is supported on a catalyst carrier selected from the group consisting of molecular sieve, silica, alumina, titanium dioxide, zirconium oxide, and niobium oxide.

5. The tantalum-containing catalyst of claim 4, wherein the supported tantalum-containing catalyst is calcined at a temperature ranging from 100° C.-1000° C.

6. The tantalum-containing catalyst of claim 4, wherein a mass ratio of said tantalum-containing catalyst to the catalyst carrier is from 0.001 to 1.

7. The tantalum-containing catalyst of claim 1, wherein the catalyst is effective in converting carbohydrate into 5-hydroxymethylfurfural (HMF).

8. The tantalum-containing catalyst of claim 7, wherein said carbohydrate is selected from the group consisting of fructose, glucose, galactose, mannose, sucrose, starch, inulin, corn juice, juice of Jerusalem artichoke tubers, and combinations thereof.

9. A method for making a tantalum-containing catalyst of claim 1, comprising the steps of:
    obtaining a solution containing a tantalum compound;
    dissolving one or more metal compounds into the solution;
    precipitating the tantalum compound with the metal compound from the solution; and
    calcining the precipitate.

10. The method of claim 9, further comprising
    mixing a catalyst carrier into the solution, wherein the carrier is selected from the group consisting of zeolite, silica, alumina, titania, zirconia, and combinations thereof.

11. The method of claim 9, wherein the one or more metal compounds is chosen from salts or oxides of nickel, tungsten, titanium, zirconium, chromium, aluminum, cobalt, platinum, palladium, ruthenium, molybdenum, vanadium, tin, niobium, and combinations thereof.

12. A tantalum-containing catalyst comprising $Ta_2O_5$—$H_3PO_4$, $Ta_2O_5/WO_3$, $Ta_2O_5/ZrO_2$, $Ta_2O_5/TiO_2$, $Ta_2O_5/Nb_2O_5$, $Ta_2O_5/V_2O_5$, or $Ta_2O_5/CeO_2$, wherein the tantalum-containing catalyst is active in catalyzing a conversion of hexose or sugar-based carbohydrates to 5-hydroxymethylfurfural,
   wherein the tantalum-containing catalyst is not supported on a catalyst carrier.

13. The tantalum-containing catalyst of claim 12,
   wherein $Ta_2O_5$—$H_3PO_4$ is produced using a method comprising reacting hydrated tantalum oxide or tantalum hydroxide with $H_3PO_4$ to obtain a precipitate and calcining the precipitate.

* * * * *